US010509090B2

(12) United States Patent
Krueger et al.

(10) Patent No.: US 10,509,090 B2
(45) Date of Patent: Dec. 17, 2019

(54) AUTOMATIC GROUPING OF MAGNETIC RESONANCE IMAGES

(71) Applicant: KONINKLIJKE PHILIPS N.V., Eindhoven (NL)

(72) Inventors: Sascha Krueger, Eindhoven (NL); Tim Nielsen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 280 days.

(21) Appl. No.: 15/548,213

(22) PCT Filed: Feb. 5, 2016

(86) PCT No.: PCT/EP2016/052550
§ 371 (c)(1),
(2) Date: Aug. 2, 2017

(87) PCT Pub. No.: WO2016/124763
PCT Pub. Date: Aug. 11, 2016

(65) Prior Publication Data
US 2018/0031666 A1 Feb. 1, 2018

(30) Foreign Application Priority Data
Feb. 6, 2015 (EP) ...................................... 15154207

(51) Int. Cl.
*G01R 33/565* (2006.01)
*G01R 33/56* (2006.01)
(Continued)

(52) U.S. Cl.
CPC ........ *G01R 33/56509* (2013.01); *A61B 5/055* (2013.01); *G01R 33/543* (2013.01);
(Continued)

(58) Field of Classification Search
CPC .................. A61B 5/055; A61N 2/1039; A61N 2005/1055; G01R 33/481; G01R 33/543;
(Continued)

(56) References Cited

U.S. PATENT DOCUMENTS 8,315,447 B2 * 11/2012 Hayes .................... A61B 5/055
128/922
9,818,200 B2 * 11/2017 Mohr ...................... G06T 7/174
(Continued)

OTHER PUBLICATIONS

Shirzadi Z et al: "An automated post processing analysis to increase (detectability of cerebral blood flow arterial spin labeling images in the presence of head motion", Pr0ceedings 0f the International Society f0r Magnetic Res0nance in Medicine, 22nd Annual Meeting and Exhibition, Milan, Italy, May 10-16, 2014, vol. 22, Apr. 28, 2014 (Apr. 28, 2014), p. 2709.
(Continued)

*Primary Examiner* — Steven L Yeninas
(74) *Attorney, Agent, or Firm* — Sherry Austin

(57) ABSTRACT

The invention provides for a method of operating a magnetic resonance imaging system. The method comprises the steps of: acquiring (200) first magnetic resonance data (142) by controlling the magnetic resonance imaging system with pulse sequence instructions (140), reconstructing (202) one or more first image (144) from the first magnetic resonance data, and assigning (204) the one or more first image to a first memory group of a set of memory groups (300). The method further comprises repeatedly performing the following steps: acquiring (206) sequential magnetic resonance data (148) by controlling the magnetic resonance imaging system with the pulse sequence instructions, reconstructing (208) one or more sequential image (150) from the sequential magnetic resonance data, computing (210) a distance measure (152) between the one or more sequential image and each of the set of memory groups, assigning (214) the
(Continued)

one or more sequential images to a chosen memory group if the distance measure between the chosen group and the one or more sequential images is within a predetermined range, creating (216) a subsequent memory group (304) in the memory if the one or more sequential images is not assigned to the chosen memory group, and assigning (218) the one or more sequential image to the subsequent memory group if the subsequent memory group is created.

15 Claims, 3 Drawing Sheets

(51) Int. Cl.
    *G01R 33/54*     (2006.01)
    *A61B 5/055*     (2006.01)
    *G01R 33/563*     (2006.01)
    *G01R 33/48*     (2006.01)
    *A61N 5/10*     (2006.01)

(52) U.S. Cl.
    CPC ......... *G01R 33/56* (2013.01); *G01R 33/5608* (2013.01); *G01R 33/56325* (2013.01); *A61N 5/1039* (2013.01); *A61N 2005/1055* (2013.01); *G01R 33/481* (2013.01)

(58) Field of Classification Search
    CPC ................ G01R 33/56; G01R 33/5608; G01R 33/56325; G01R 33/56509
    USPC .......................................................... 324/309
    See application file for complete search history.

(56) References Cited

U.S. PATENT DOCUMENTS

| | | |
|---|---|---|
| 2009/0226060 A1 | 9/2009 | Gering et al. |
| 2012/0281897 A1 | 11/2012 | Razifar et al. |
| 2014/0219531 A1* | 8/2014 | Epstein ............ G01R 33/56308 382/131 |
| 2014/0296702 A1* | 10/2014 | Griswold ........... G01R 33/3614 600/416 |
| 2015/0243023 A1* | 8/2015 | Fan .................... G01R 33/4806 382/131 |

OTHER PUBLICATIONS

Daenzer Stefan et al: "VoIH0G: A volumetric object recognition approach based on bivariate histograms of oriented gradients for vertebra detection in cervical spine MRI",Medical Physics, AIP, Melville, NY, US, vol. 41, No. 8, Jul. 31, 2014.
Ülasï Prg A et al: "Dissimilarity-Based Detection of Schizophrenia",Brain DecOding: Pattern Recognition Challenges in NeurOimaging (WBD), 2010 First Workshop 0n, IEEE, Piscataway, NJ, USA, Aug. 22, 2010 (Aug. 22, 2010), pp. 32-35.
Luchtenberg Anne et al: "Early detection of Alzheimer's disease using histograms in a dissimilarity-based classification framework",PrOgress in BiOmedical Optics and Imaging, SPIE—InternatiOnal SOciety or Optical Engineering, Bellingham, WA, US, vol. 9035, Mar. 18, 2014 (Mar. 18, 2014), pp. 903502-903502.
Warfield S: "Fast k-NN classification for multichannel image data", Pattern Recognition Letters, Elsevier, Amsterdam, NL,vol. 17, No. 7, Jun. 10, 1996 (Jun. 10, 1996), pp. 713-721.
Vedam et al "Acquiring a Four Dimensional Computed Tomography Dataset Using an External Respiratory Signal" Physics in Med. and Bio. 48 (2003) p. 45-62.

* cited by examiner

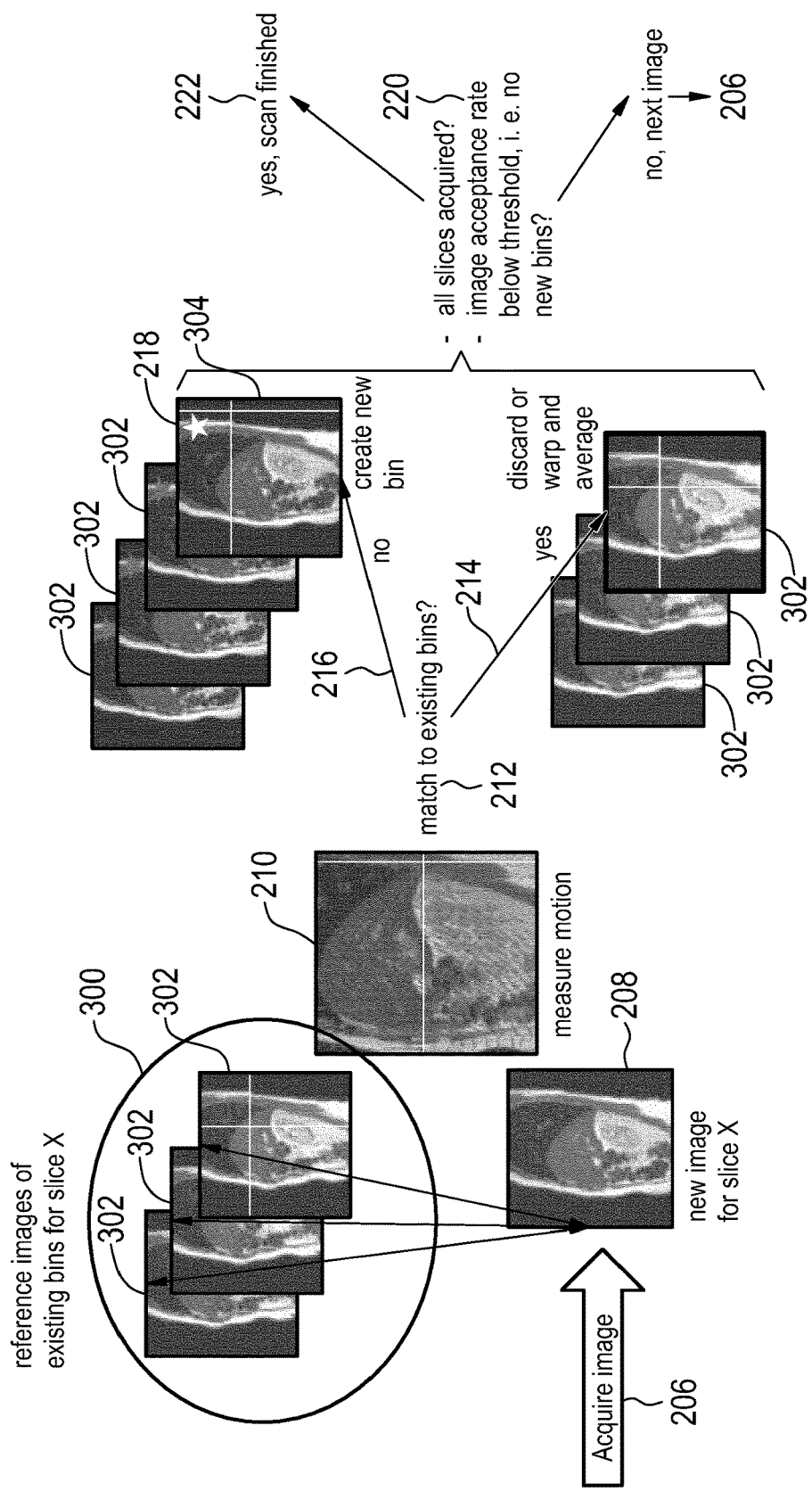

AUTOMATIC GROUPING OF MAGNETIC RESONANCE IMAGES

CROSS REFERENCE TO RELATED APPLICATIONS

This application is a U.S. national phase application of International Application No. PCT/EP2016/052550, filed on Feb. 5, 2016, which claims the benefit of EP Application Serial No. 15154207.3 filed on Feb. 6, 2015 and is incorporated herein by reference.

TECHNICAL FIELD

The invention relates to magnetic resonance imaging, in particular to assigning images to groups which characterize motion.

BACKGROUND OF THE INVENTION

The main clinical purpose of Four Dimensional Magnetic Resonance Imaging (4D MRI) is treatment margin definition for external beam radiation therapy. Normally, 4D MRI data acquisition methods are based on usage of sensor signals indicative of the state/phase of the motion to be resolved. E.g. in respiratory 4D MRI a respiratory belt or MRI based navigators are used to detect a requested motion state and to trigger the acquisition.

However, especially in the abdominal region, motion can be composed of periodic and singular motion and the respective motion space to be covered is a-priori less known, e.g. in some regions peristaltic motion may outweigh the respiratory motion (e.g. pelvis) while in others respiratory motion will be predominant (e.g. upper abdomen). As a consequence, utilization of one motion sensor is often insufficient for treatment planning, since a more comprehensive measurement of the motion statistics is desirable. An additional disadvantage of classical 4D MRI is the strongly decreasing scan efficiency towards the end of the scan and the resulting bio-feedback.

United States Patent Application publication US 2012/0281897 A1 discloses a method for reducing, in an image, motion related imaging artifacts includes obtaining an image dataset of a region of interest, generating a plurality of intermediate images using the image dataset, applying a multivariate data analysis technique to the plurality of the intermediate images to generate motion information, sorting the intermediate images into a plurality of bins based on the motion information, and generating an image of the region of interest using at least one of the plurality of bins.

SUMMARY OF THE INVENTION

The invention provides for a magnetic resonance imaging system, a computer program product and a method in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a magnetic resonance imaging system for acquiring magnetic resonance data from a subject. The magnetic resonance imaging system comprises a memory for storing machine-executable instructions and pulse sequence instructions. The pulse sequence instructions cause the magnetic resonance imaging system to acquire the magnetic resonance data according to a magnetic resonance imaging protocol. The magnetic resonance imaging system further comprises a processor for controlling the magnetic resonance imaging system. Execution of the machine-executable instructions causes the processor to acquire first magnetic resonance data by controlling the magnetic resonance imaging system with the pulse sequence instructions. Execution of the machine-executable instructions further causes the processor to reconstruct one or more first image from first magnetic resonance data. Execution of the machine-executable instructions further cause the processor to assign the one or more first image to a first memory group of a set of memory groups.

Execution of the machine-executable instructions causes the processor to repeatedly reacquire the sequential magnetic resonance data by controlling the magnetic resonance imaging system with the pulse sequence instructions. Execution of the machine-executable instructions further causes the processor to repeatedly reconstruct one or more sequential image from the sequential magnetic resonance data. Execution of the machine-executable instructions further cause the processor to repeatedly compute a distance measure between the one or more sequential image and each of the set of memory groups. The term 'distance measure' may also be represented by the term 'distance metric'. The distance measure may also refer to what is known as a similarity measure or metric. Execution of the machine-executable instructions further cause the processor to assign the one or more sequential images to a chosen memory group if the distance measure between the chosen group and the one or more sequential images is within a predetermined range. A chosen memory group is an existing memory group.

Each of the memory groups may have a predetermined range of values that is assigned to it or determined from it. If the distance measure for the one or more sequential images is within the predetermined range for the chosen memory group then the one or more sequential images are assigned to this chosen memory group. The chosen memory group is one of the set of memory groups. Execution of the machine-executable instructions further cause the processor to create a subsequent memory group in the memory if the one or more sequential images is not assigned to the chosen memory group. In other words the subsequent memory group is created if the one or more sequential images do not fit well or are not clustered according to the predetermined ranges. Execution of the machine-executable instructions further causes the one or more sequential image to be assigned to the subsequent memory group if the subsequent memory group has been created.

The steps performed by the machine-executable instructions define a process where the images are assigned to various memory groups on the fly. It is not necessary to have the memory groups defined in advance as they are created as dissimilar images are acquired and assigned to the subsequent memory group.

The magnetic resonance protocol could for example be a single-shot turbo spin echo or a Turbo Field Echo multi-slice acquisition.

In some examples the one or more first image and the one or more sequential images are simply a single image. For example "one or more sequential image" may be replaced with "a sequential image." "One or more first image" may be replaced with "a first image."

If there are multiple images such as there are multiple first images and multiple sequential images there may be several different cases. First the same image may be acquired repeatedly using the pulse sequence. That is to say the image of the same slice is acquired repeatedly. In other instances the multiple images may be from different slices. In this case the distance measure is calculated for each of the individual slices.

The term "set of memory groups" may be understood in different terms depending upon how it is implemented. For example, in some cases the set of memory groups may be defined by entries in a database. For instance various images may be stored within various records of a database system. In other instances the images are stored in the computer memory or storage and are simply referenced by a list of which images are with which group. In yet other examples, pointers or other structures are used to define which images belong to which of the set of memory groups.

The memory group may also be understood in terms of what is known as a bin. For example, the problem of assigning the images to the various memory groups may be understood in terms of a sorting problem.

The number of memory groups which are used does not need to be fixed at the beginning. Instead, an image based criterion is used to decide for each newly acquired image if it fits into an existing group or if a new group needs to be created.

The measurement time also does not need to be fixed. Several criteria or combinations of criteria can be used to terminate the acquisition: total scan duration limit or determine if the information gain is too low (i.e. all acquired images for the past seconds belong to an already existing memory group).

Another implication is that the technique does not necessarily require acquisition of a reference image.

What may be used instead is an image based measure for similarity and a criterion when to create a subsequent group. The technique could possibly be applied as follows: The first image that is acquired cannot be compared to anything else therefore it forms the first group. The second image and all others that follow is compared to all existing groups and it is put into a group if it is similar enough. If it is not similar to any group then a subsequent group is created containing this image.

The distance measure may be implemented in different ways.

One fundamental measure may be the difference between two images:

I.e. a mapping assigning a real number d(A,B) to a pair of images A, B with d(A,A)=0.

This difference measure can be defined in different ways: sum absolute differences of pixel values $d(A,B)=\text{sum}_i (A_i-B_i)^2$ Calculate correlation of all pixel values between A and B. Compared to 1 this has the advantage that a global scaling of intensity between A and B does not influence the measure.

Even better, because local intensity fluctuations do not matter: divide each image into a number of small patches and calculate a local correlation for each patch, then average the correlation values for all patches.

These are just some examples of simple difference measures, which may be used in image processing. They are also independent of the cause of the difference between image A and B.

A different distance measure that does not depended on a difference between images is described below. The difference measure is a measure of geometric displacements. One way to do this is to use an image transformation Ta which depends on a set of parameters a and which can produce a new image $B'=T_a(B)$. Then for any two images the optimal transformation parameters $a_{opt}(A,B)$ can be defined by an optimization $a_{opt}(A,B)=\min_a d(A,T_a(B))$ (where d is one of the simple difference measures from above that do not need a model). Finally, the difference $d_T$ between images A and B is defined by mapping the parameter vector $a_{opt}$ to a real number $d_T=s(a_{opt}(A,B))$.

Advantage of this model based difference definition may be that the influence of factors which change the image but which are not of interest can be reduced by a proper choice of model.

To make this more concrete: The transformation model for 2D images could be image interpolation where the Cartesian pixel coordinates i',j' of image B' are mapped to coordinates i,j in a distorted coordinate system in the source image. This distorted coordinate system could be defined by e.g. spline interpolation based on a set of m×n control points on a rectangular grid. Then the parameter vector a which describes the transformation is the set of m×n displacement vectors of the control points. s could be the average magnitude of all displacements.

One alternative was of defining an image difference or difference measure is to transform both images A, and B into something else and then quantify the difference between the results of the transform: $d(A,B):=d_F(F(A),F(B))$. E.g. the transformation F could be to automatically detect landmarks on image A and B and $d_F$ the average displacement between corresponding landmarks. Or, F could be to automatically segment a contour of an organ, and $d_F$ a difference measure for contours.

Finally, the difference measure between an image A and a group of images G in claim 1 could for example be defined based on the difference between two images d(A,B): e.g. $d(A,G)=\min_{(B\ in\ G)} d(A,B)$ or "max" or "mean" instead of "min."

In another embodiment execution of the machine-executable instructions causes the processor to receive anatomical identification data. The anatomical identification data is descriptive of one or more anatomical structures within the subject. For example the anatomical identification data may be useful for segmenting or identifying anatomical landmarks or fitting an anatomical model to the subject. Execution of the machine-executable instructions further causes the processor to calculate location data for each of the set of memory groups. The location data is descriptive of the location of the one or more anatomical structures within the images of each of the set of memory groups. For example the anatomical identification data may be registered to the images within each of the set of memory groups. This then provides a reference to the position of these anatomical identification landmarks or data with respect to each of the images.

Execution of the machine-executable instructions further causes the processor to calculate motion statistics for the one or more anatomical location using the location data for each of the set of memory groups. This embodiment may be beneficial because it may provide statistics as to the location of a particular portion of the subject as a function of time. For example, if an anatomical structure which is desired to be irradiated or sonicated is identified by the anatomical identification data knowing the location of it as a function of time may help the decision as to where to direct energy into the subject. Likewise, if there are anatomical structures within the subject that need to be protected from being treated or irradiated or sonicated, it may be beneficial to know how these structures are positioned as a function of time or for a fraction of the time.

The motion statistics may be calculated in different ways. For example, some of the memory groups may have more images within them. This may be used to give a higher weighting to the various positions for that particular memory group.

In some examples, each of the set of memory groups may be averaged or an average image may be determined and then this is used to determine the motion statistics. Even if an average image is used, then the number of images in the particular set of memory groups may still be used to weight the value or influence of that particular average image.

In another embodiment each of the set of memory group comprises images.

In another embodiment execution of the machine-executable instructions further cause the processor to receive a treatment plan. Execution of the machine-executable instructions further causes the processor to calculate radiotherapy instructions for controlling a radiotherapy system using the treatment plan and the motion statistics.

In another embodiment the magnetic resonance imaging system comprises the radiotherapy system and execution of the machine-executable instructions causes the processor to control the radiotherapy system using the radiotherapy instructions.

In another embodiment the distance measure is calculated for one or more region of interest. Limiting the distance measure to a particular region of interest may be of benefit. For example, if a region of the subject is imaged where the anatomy is not static or rigid, limiting the distance measure to a particular region or regions of interest may improve the quality of the motion statistics of this area.

For example multiple distance measures could be combined in different ways. The average of multiple distance measures could be used. The maximum of multiple distance measures could be used. The minimum of multiple distance measures could be used. The median of multiple distance measures could be used.

The multiple distance measures could be combined in a weighted average or a weighted sum of the multiple distance measures. For example if there were two distance measures, one soft tissue in the abdominal cavity and one for tissue surrounding the ribs one could give weight the sum of the distance measures such that the soft tissue affects the overall distance measure more.

In another embodiment the one or more region of interest is predefined. For example the region of interest may be defined by anatomical data or other information which is received.

In another example, the one or more region of interest is defined by segmenting the images and determining them automatically. In other examples the one or more region of interest may be received by data that is input into a user interface of the magnetic resonance imaging system.

In another embodiment execution of the machine-executable instructions further cause the processor to identify the one or more region of interest according to any one of the following: by using an image segmentation algorithm, by receiving a manual image segmentation, and by propagating a reference segmentation using the distance measure.

In another embodiment the one or more region of interest comprises at least one rigid region of interest and at least one deformable region of interest. This may be beneficial in situations where there are rigid structures and moveable structures within a subject. For example, if the abdominal cavity of a subject is imaged, areas such as the ribs and the spine will be rigid and will move as a rigid body. Organs within the abdominal cavity however, may be free to slide and move relative to these fixed structures. Defining different types of interest such as rigid and deformable within the same image may result in improved grouping of the images into the various sets of memory groups.

In another embodiment execution of the machine-executable instructions further cause the processor to calculate an average difference mapping for each of the set of memory groups. For example the difference map could be an optical flow or displacement map with respect to a reference image or a group in some examples.

In one example the "average difference mapping" could be the average of all $a_{opt}(A,B)$ where A is from the reference group and B is from the selected memory group.

In another embodiment execution of the machine-executable instructions further cause the processor to calculate an average difference mapping for each of the set of memory groups with respect to a chosen reference group. The chosen reference group is one of the set of memory groups. For example the chosen reference group may have an average image which is calculated. The average difference mapping for each of the set of memory groups may be calculated with respect to this average image.

In another embodiment execution of the machine-executable instructions further cause the processor to calculate a difference mapping between each image in a selected memory group chosen from the set of memory groups and the average distance mapping. Execution of the machine-executable instructions further cause the processor to select from the selected memory group a selected image that minimizes a statistical measure applied to the difference mapping. Execution of the machine-executable instructions further cause the processor to store the selected image as an average image for the selected memory group. In this example the image which is essentially the closest to the average is selected as the average image.

The statistical measure could for example be the minimum average displacement from the average distance map.

In another embodiment execution of the machine-executable instructions further causes the processor to calculate a transformed image for the selected image in the selected memory group using the average difference mapping. The transformed image is stored as the average image for the selected memory group. In this example the average image is still the image which is closest to the average; however, in this particular example the average image is transformed so that it more closely matches the average.

In another embodiment execution of the machine-executable instructions further cause the processor to calculate a difference mapping between each image in a selected memory group chosen from the set of memory groups and the average difference mapping. Execution of the machine-executable instructions further cause the processor to calculate a transformed image for each image in the selected memory group using the difference mapping for each image. Execution of the machine-executable instructions further cause the processor to calculate an average image for the selected memory group by averaging each transformed image of the selected memory group. In this example the average difference mapping is calculated. This is used to determine how far each image is from the average. Each image in the memory group is then transformed so that it more accurately matches the average. These transformed images are then averaged to make an average image which accurately represents the average values of the selected memory group.

In another embodiment execution of the machine-executable instructions further cause the processor to render a time-dependent image using the average image for each of the set of memory groups. The time-dependent image may for instance take different forms. It may take the form of an animation or it may also display the location of different anatomical references or locations within the subject that are weighted as a function of time. For example the location of a particular organ could be blurred to represent its location as a function of time.

In another embodiment the distance measure comprises any one of the following: an average displacement, an identification of the homogeneous motion field, identification of a local motion field and combinations thereof.

In another embodiment the one or more reference image is a single reference image of a slice. The one or more sequential image is a single sequential image of the slice.

In another aspect the invention provides for a computer program product comprising machine-executable instructions for execution by a processor controlling a magnetic resonance imaging system that is configured for acquiring magnetic resonance data from a subject. The magnetic resonance imaging system comprises a memory for storing pulse sequence instructions. The pulse sequence instructions cause the magnetic resonance imaging system to acquire the magnetic resonance data according to a magnetic resonance imaging protocol. Execution of the machine-executable instructions causes the processor to acquire first magnetic resonance data by controlling the magnetic resonance imaging system with the pulse sequence instructions.

Execution of the machine-executable instructions further causes the processor to reconstruct one or more first image from the first sequential magnetic resonance data. Execution of the machine-executable instructions further cause the processor to repeatedly reacquire the sequential magnetic resonance data by controlling the magnetic resonance imaging system with the pulse sequence instructions. Execution of the machine-executable instructions further causes the processor to repeatedly reconstruct one or more sequential image from the sequential magnetic resonance data. Execution of the machine-executable instructions further cause the processor to repeatedly compute a distance measure between the one or more sequential image and each of the set of memory groups.

Execution of the machine-executable instructions further cause the processor to repeatedly assign the one or more sequential images to a chosen memory group if the distance measure between the chosen group and the one or more sequential images is within a predetermined range. The chosen memory group is one of the set of memory groups. Execution of the machine-executable instructions further cause the processor to repeatedly create a subsequent memory group in the memory if the one or more sequential image is not assigned to the chosen memory group. Execution of the machine-executable instructions further cause the processor to repeatedly assign the one or more sequential image to the subsequent memory group if the subsequent memory group is created.

In another aspect the invention provides for a method of operating a magnetic resonance imaging system configured for acquiring magnetic resonance data from a subject. The method comprises the step of acquiring first magnetic resonance data by controlling the magnetic resonance imaging system with pulse sequence instructions. The pulse sequence instructions cause the magnetic resonance imaging system to acquire the magnetic resonance data according to a magnetic resonance imaging protocol. The method further comprises the step of reconstructing one or more first image from the first magnetic resonance data. The method further comprises the step of assigning the one or more first image to a first memory group of a set of memory groups. Each of the set of memory group comprises images. The method further comprises the step of repeatedly reacquiring the sequential magnetic resonance data by controlling the magnetic resonance imaging system with the pulse sequence instructions. The method further comprises the step of repeatedly reconstructing one or more sequential image from the sequential magnetic resonance data. The method further comprises the step of repeatedly computing a distance measure between the one or more sequential image and each of the set of memory groups. The method further comprises the step of repeatedly assigning the one or more sequential images to a chosen memory group if the distance measure is between the chosen group and the one or more sequential images within a predetermined range. The chosen memory group is one of the set of memory groups. The method further comprises the step of repeatedly creating a subsequent memory group in the memory if the one or more sequential image is not assigned to the chosen memory group. The method further comprises the step of assigning the one or more sequential image to the subsequent memory group if the subsequent memory group is created.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIG. 3 shows a flow chart which illustrates a further example of a method of operating the magnetic resonance imaging system of FIG. 1.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
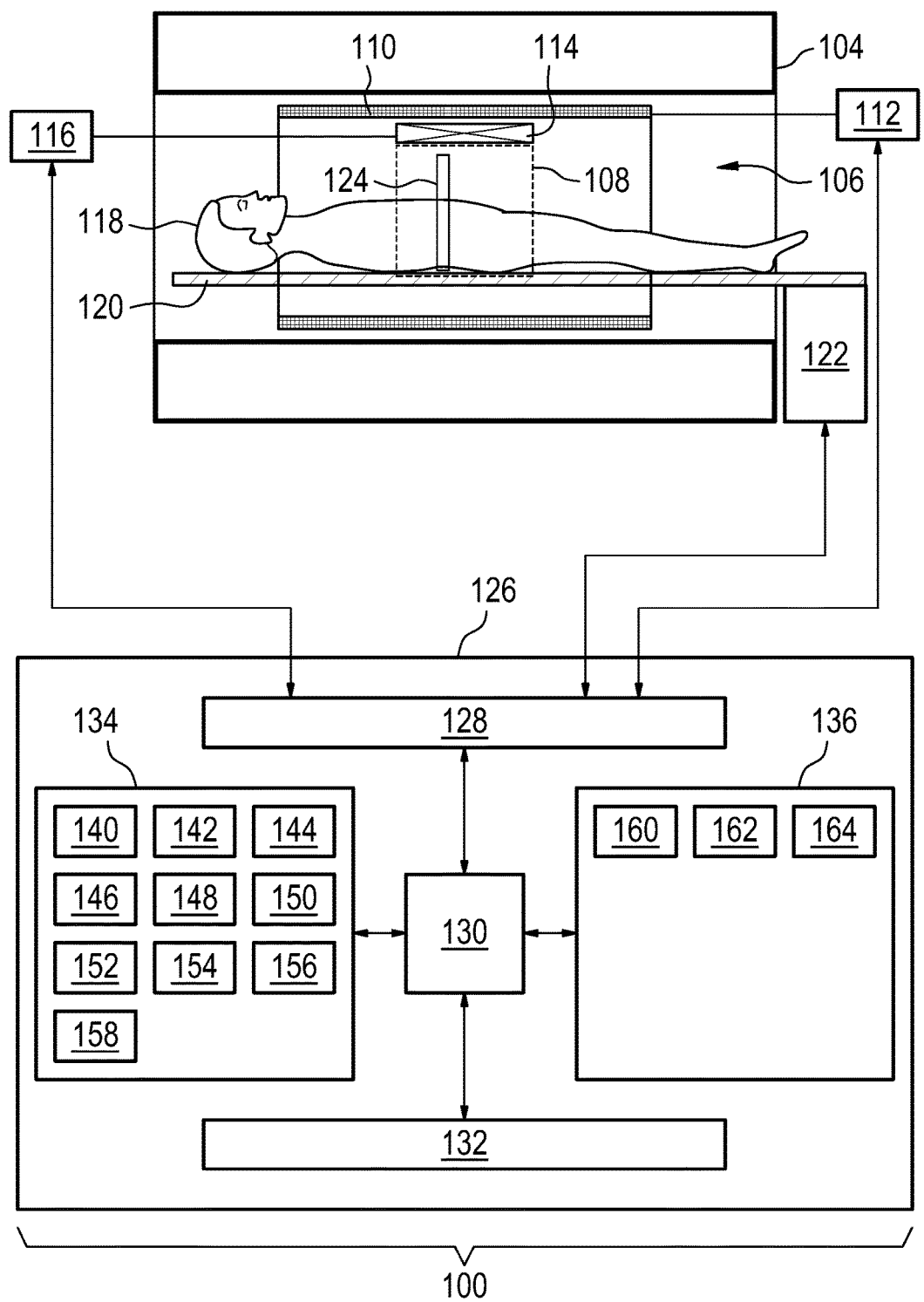
FIG. 1 illustrates an example of a magnetic resonance imaging system.

FIG. 1 shows an example of a magnetic resonance imaging system 100 with a magnet 104. The magnet 104 is a superconducting cylindrical type magnet 104 with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet, there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels.

Within the imaging zone 108 can be seen a box labeled 124. This shows the position of a slice 124 that is used to acquire magnetic resonance image data from the abdominal region of the subject 118.

Within the bore 106 of the magnet 104 there is a subject support 120 which is attached to an optional actuator 122 that is able to move the subject support and the subject 118 through the imaging zone 108 The transceiver 116, the magnetic field gradient coil power supply 112 and the actuator 122 are all see as being connected to a hardware interface 128 of computer system 126.

The contents of the computer storage 134 and the computer memory 136 may be interchangeable. In some examples the contents of the computer storage 134 may be duplicated in the computer memory 136.

The computer storage is shown as having pulse sequence instructions 140 that enable the processor 130 to control the components of the magnetic resonance imaging system 100 to acquire magnetic resonance data. The pulse sequence instructions 140 were used to acquire first magnetic resonance data 142 and to repeatedly acquire the sequential magnetic resonance data 148. Both 142 and 148 are shown as being stored in the computer storage 134. The computer storage 134 is further shown as containing one or more first image 144 that was reconstructed from the first magnetic resonance data 142. The computer storage 134 is further shown as containing an image database 146 which is used to store the groups of images.

The database 146 may take different forms. For example in some examples the image database may be a relational database and may contain other information about images which can be queried. For example very statistical measures and operations which are performed on various images can be stored in the image database 146 so they do not need to be recalculated. The computer storage 134 is further shown as containing the one or more sequential image 150 that was reconstructed from the sequential magnetic resonance data 148. The computer storage 134 is further shown as containing a measure distance 152 that has been calculated on the one or more sequential image 150. The distance measure 152 will then be used to compare two groups within the image database 146 and either to place the one or more sequential image 150 into an existing group or create a subsequent group within the database 146.

The computer storage 134 also shows several optional entries. There may for example be anatomical identification data 154 that has been received by the computer 126. This may be used to segment or otherwise process the one or more sequential image 150 to obtain location data 156 of anatomical references or landmarks within the subject 118. The images in the image database 146 have this location data 156 analyzed and motion statistics 158 can be generated.

The computer memory 136 is shown as containing a control module 160. The control module enables the processor 130 to control the operation and function of the magnetic resonance imaging system 100. For example the control module 160 may enable the processor 130 to control the acquisition of magnetic resonance data using the pulse sequence instructions 140. The computer memory 136 is further shown as containing an image reconstruction module 162. The image reconstruction module 162 contains computer-executable code which enables the processor 130 to reconstruct magnetic resonance images 144, 150 from magnetic resonance data 142, 148. The computer memory 136 is further shown as containing image processing module 164.

The image processing module 164 enables the processor 130 to perform various image processing techniques such as locating the anatomical references, using the anatomical identification data 154, comparing different images or groups of images to calculate the distance measure 152, and to perform other tasks such as generating motion statistics 158. The image processing module 164 in some instances may also contain modules or portions which enable the processor 130 to identify and calculate the distance measure 152 based on different regions of interest within images.

Figure 2:
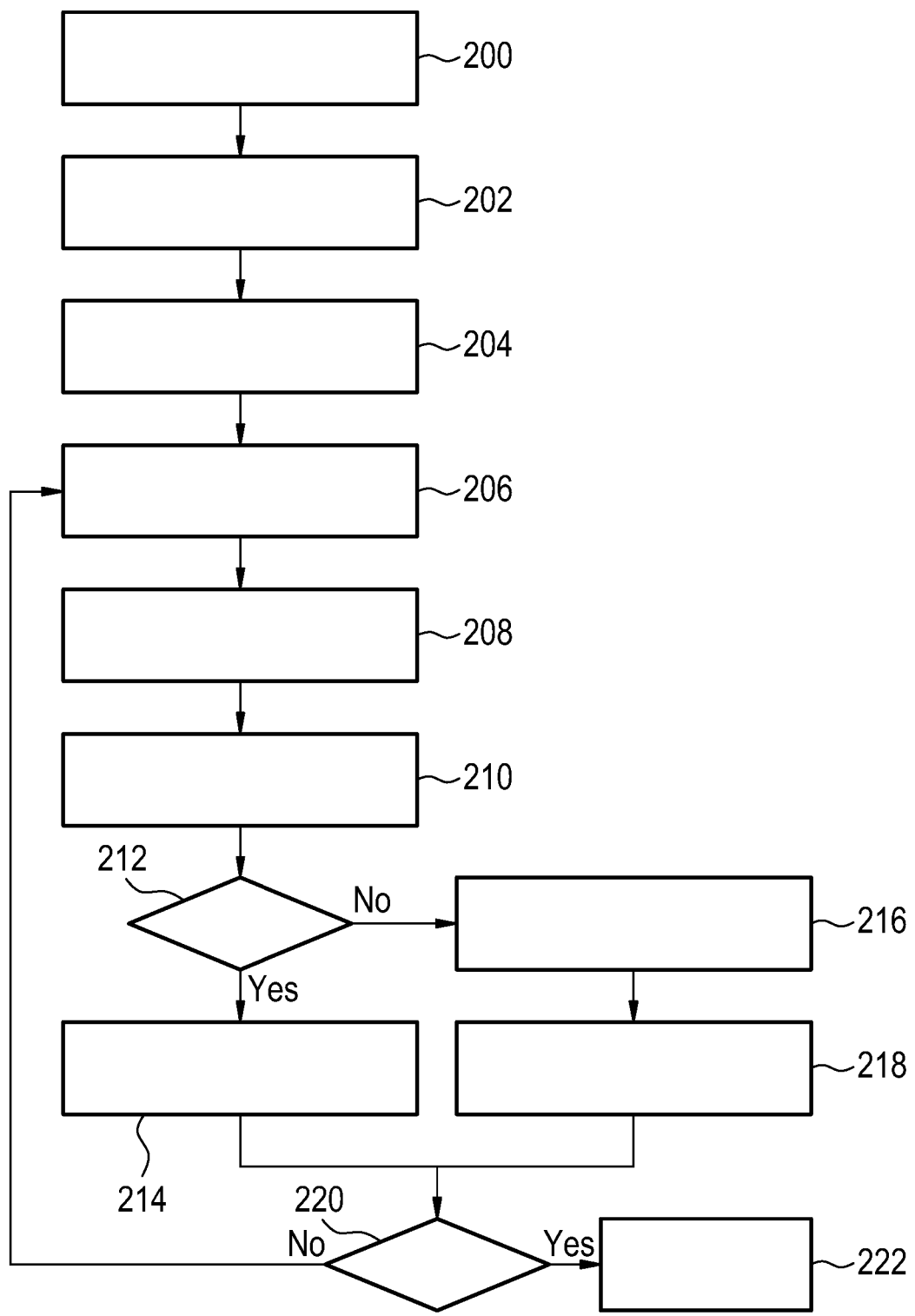
FIG. 2 shows a flow chart which illustrates an example of a method of operating the magnetic resonance imaging system of FIG. 1.

FIG. 2 shows a flowchart which illustrates an example of a method of operating the magnetic resonance imaging system 100 of FIG. 1. First in step 200 the first magnetic resonance data 142 is acquired by controlling the magnetic resonance imaging system 100 with the pulse sequence instructions 140. Next in step 202 the first magnetic resonance data 142 is reconstructed into the one or more first image 144. Next in step 204 the one or more first image 144 is assigned to a first memory group of a set of memory groups. In this example of FIG. 1 the one or more first image is assigned to a first group in the image database 146. Next in step 206 the sequential magnetic resonance data 148 is acquired by controlling the magnetic resonance imaging system 100 with the pulse sequence instructions 140. In step 208 the one or more sequential image 150 is reconstructed from the sequential magnetic resonance data 148.

Next in step 210 a distance measure 152 is calculated between the one or more sequential image 150 and each of the set of memory groups. Next in step 212 the distance measure is compared to the distance measures or range of distance measures for each of the set of memory groups. The question in box 212 is: does the distance measure 152 fit within one of the existing memory groups? If the answer is yes then the method proceeds to step 214. If the answer is no then the method proceeds to step 216. In step 214 the one or more sequential image 150 is assigned to a chosen memory group if the distance measure 152 between the chosen group and the one or more sequential image is within a predetermined range. In step 216 the processor 130 instructs the database 146 to create a subsequent memory group. Next in step 218 the one or more sequential image 150 is assigned to the subsequent memory group. Both steps 214 and 218 go to step 220. Step 220 is a question, whether the acquisition of data is finished. If the answer is no, then the method returns back to step 206. If the answer is yes then the method proceeds to step 222. In step 222 the method ends.

A 4D MRI method is presented that in some examples may work without sensor and a-priori assumptions about the expected motion components and is thus capable of capturing full motion statistics of a target region. Instead of using trigger mechanisms to detect motion states and perform scanning only when a desired state has been reached, it is proposed to acquire the slices of the volume with highest possible duty-cycle (un-triggered) and to use real-time image processing to sort individual slices of a 4D scan in to respective bins of a 4D MRI scan. The images corresponding to one bin may undergo residual matching so that the majority of the acquired images in one bin can be averaged for highest possible SNR in the images. Images or image sub-regions belonging to one bin that cannot be matched with sufficient accuracy (measured e.g. as correlation to reference image of the bin (first or mean image)) can be discarded. For a given slice number, bins may be continuously created depending on the measured motion, i.e. if the newly acquired image differs more from the already present bins by a user-defined value (applications-specific displacement unit to be resolved). The scan finalization criterion is chosen such that an optimum compromise of motion state coverage and scan time is provided: The scan is defined as completed if all slices have been acquired and the image acceptance or subsequent bin creation rate is below a definable threshold.

In case 4D volumes are desired, the motion continuity in space and time can be used to sort the acquired images into the individual volumes.

FIG. 3 shows a graphical representation of a method of operating the magnetic resonance imaging system 100 of FIG. 1. First in step 206 an image is acquired. This is then reconstructed into the image 208. The circle 300 represents the set of memory groups. Within the set of memory groups 300 are a number of existing memory groups 302. In step 210 the image 208 is compared to the existing memory groups 302. This is used to calculate the difference measure. In this example the distance measure is an optical flow. The distance measure is then compared in step 212 to see if it matches an existing bin or memory group or not. If it does, yes, then the image is associated with an existing memory group 302. If not, then step 216 is performed as previously described. A subsequent memory group 304 is created and the image 208 is assigned to the subsequent memory group 304. After step 214, 216 and associated steps have been completed the method proceeds to step 220. If all slices are acquired then the scan finishes 222. If not then the method returns back to step 206 and the next image is acquired.

In the Figure there is an alternative to the question in step 220, if the average acceptance rate is below a particular threshold then the method can also end. For example, if the method has performed a set number of cycles and no subsequent bins or memory groups have been added then it may be considered that the motion of the subject has been completely characterized and the method can stop.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance system
104 magnet
106 bore of magnet
108 measurement zone or imaging zone
110 magnetic field gradient coils
112 magnetic field gradient coil power supply
114 radio-frequency coil
116 transceiver
118 subject
120 subject support
122 actuator
124 slice
126 computer system
128 hardware interface
130 processor
132 user interface
134 computer storage
136 computer memory
140 pulse sequence instructions
142 first magnetic resonance data
144 one or more first image
146 image database
148 sequential magnetic resonance data
150 one or more sequential image
152 distance measure
154 anatomical identification data
156 location data
158 motion statistics
160 control module
162 image reconstruction module
164 image processing module
200 acquire first magnetic resonance data by controlling the magnetic resonance imaging system with the pulse sequence instructions
202 reconstruct one or more first image from the reference magnetic resonance data
204 assign the one or more first image to a first memory group of a set of memory groups
206 acquire the sequential magnetic resonance data by controlling the magnetic resonance imaging system with the pulse sequence instructions
208 reconstruct one or more sequential image from the sequential magnetic resonance data
210 compute a distance measure between the one or more sequential image and each of the set of memory groups
212 does the image belong to an existing group?
214 assign the one or more sequential images to a chosen memory group if the distance measure between the chosen group and the one or more sequential images is within a predetermined range
216 create a subsequent memory group in the memory if the one or more sequential images is not assigned to the chosen memory group
218 assign the one or more sequential image to the subsequent memory group if the subsequent memory group is created
220 Have all images been acquired?
300 set of memory groups
302 existing memory group
304 subsequent memory group

The invention claimed is:

1. A magnetic resonance imaging system for acquiring magnetic resonance data from a subject and further configured for creating a set of memory groups comprising a plurality of memory groups and assigning one or more acquired images to each of the memory groups, wherein the magnetic resonance imaging system comprises:
 a memory for storing machine executable instructions and pulse sequence instructions, wherein the pulse sequence instructions cause the magnetic resonance imaging system to acquire the magnetic resonance data according to a magnetic resonance imaging protocol;
 a processor for controlling the magnetic resonance imaging system, wherein execution of the machine executable instructions causes the processor to:
 acquire first magnetic resonance data by controlling the magnetic resonance imaging system with the pulse sequence instructions; and
 reconstruct one or more first images from the first magnetic resonance data;
 assign the one or more first images to a first memory group wherein execution of the machine executable instructions cause the processor to repeatedly:
 acquire sequential magnetic resonance data by controlling the magnetic resonance imaging system with the pulse sequence instructions;
 reconstruct one or more sequential images from the sequential magnetic resonance data;
 compute a distance measure between the one or more sequential images and each of the set of memory groups;
 assign the one or more sequential images to an existing memory group if the distance measure between the existing memory group and the one or more sequential images is within a predetermined range;
 create a subsequent memory group if the one or more sequential images is not assigned to the existing memory group; and
 assign the one or more sequential images to the subsequent memory group if the subsequent memory group is created.

2. The magnetic resonance imaging system of claim 1, wherein the execution of the machine executable instructions causes the processor to:
 receive anatomical identification data, descriptive of one or more anatomical structure within the subject;
 calculate location data or each for the set of memory groups, wherein the location data is descriptive of the location of the one or more anatomical structure within the images of each of the set of memory groups; and
 calculate motion statistics for the one or more anatomical location using the location data for each of the set of memory groups.

3. The magnetic resonance imaging system of claim 2, wherein execution of the machine executable instructions further causes the processor to:
- receive a treatment plan; and
- calculate radio therapy instructions for controlling a radiotherapy system using the treatment plan and the motion statistics.

4. The magnetic resonance imaging system of claim 1, wherein the distance measure is calculated within one or more region of interest.

5. The magnetic resonance imaging system of claim 4, wherein the one or more region of interest is predefined.

6. The magnetic resonance imaging system of claim 5, wherein execution of the machine executable instructions further cause the processor to identify the one or more region of interest according to any one of the following: by using an image segmentation algorithm, by receiving a manual image segmentation, and by propagating a reference segmentation using the distance measure.

7. The magnetic resonance imaging system of claim 5, wherein the one or more region of interest comprises at least one rigid region of interest and at least one deformable region of interest.

8. The magnetic resonance imaging system of claim 1, wherein execution of the machine executable instructions further cause the processor to calculate an average difference mapping for each of the set of memory groups with respect to a chosen reference group, wherein the chosen reference group is one of the set of memory groups.

9. The magnetic resonance imaging system of claim 8, wherein execution of the machine executable instructions further causes the processor to:
- calculate a difference mapping between each image in a selected memory group chosen from the set of memory groups and the average distance mapping; and
- select from the selected memory group a selected image that minimizes a statistical measure applied to the difference mapping;
- store the selected image as an average image for the selected memory group.

10. The magnetic resonance imaging system of claim 9, wherein execution of the machine executable instructions further causes the processor to calculate a transformed image for the selected image in the selected memory group using the average difference mapping, and wherein the transformed image is stored as the average image for the selected memory group.

11. The magnetic resonance imaging system of claim 8, wherein execution of the machine executable instructions further causes the processor to:
- calculate a difference mapping between each image in a selected memory group chosen from the set of memory groups and the average difference mapping;
- calculate a transformed image for each image in the selected memory group using the difference mapping for each image; and
- calculate an average image for the selected memory group by averaging each transformed image of the selected memory group.

12. The magnetic resonance imaging system of claim 8, wherein execution of the machine executable instructions causes the processor to render a time dependent image using the average image for each of the set of memory groups.

13. The magnetic resonance imaging system of claim 1, wherein the distance measure comprises any one of the following: an average displacement, an identification of a homogeneous motion field, an identification of a local motion field, and combinations thereof.

14. A non-transitory computer readable medium comprising machine executable instructions for execution by a processor controlling a magnetic resonance imaging system for acquiring magnetic resonance data from a subject further configured for creating a set of memory groups comprising a plurality of memory groups and assigning one or more acquired images to each of the memory groups wherein the magnetic resonance imaging system comprises a memory for storing pulse sequence instructions, wherein the pulse sequence instructions cause the magnetic resonance imaging system to acquire the magnetic resonance data according to a magnetic resonance imaging protocol, wherein execution of the machine executable instructions causes the processor to:
- acquire first magnetic resonance data by controlling the magnetic resonance imaging system with the pulse sequence instructions; and
- reconstruct one or more first images from the first magnetic resonance data;
- assign the one or more first images to a first memory group;
- wherein execution of the machine executable instructions cause the processor to repeatedly:
- acquire sequential magnetic resonance data by controlling the magnetic resonance imaging system with the pulse sequence instructions;
- reconstruct one or more sequential images from the sequential magnetic resonance data;
- compute a distance measure between the one or more sequential images and each of the set of memory groups;
- assign the one or more sequential images to an existing memory group if the distance measure between the existing memory group and the one or more sequential images is within a predetermined range;
- create a subsequent memory group in the memory if the one or more sequential images is not assigned to the chosen memory group; and
- assign the one or more sequential image to the subsequent memory group if the subsequent memory group is created.

15. A method of operating a magnetic resonance imaging system configured for acquiring magnetic resonance data from a subject, further configured for creating a set of memory groups comprising a plurality of memory groups and assigning one or more acquired images to each of the memory groups, wherein the method comprises:
- acquiring first magnetic resonance data by controlling the magnetic resonance imaging system with the pulse sequence instructions; and
- reconstructing one or more first images from the first magnetic resonance data;
- assigning the one or more first images to a first memory group; wherein execution of the machine executable instructions cause the processor to repeatedly:
- acquiring sequential magnetic resonance data by controlling the magnetic resonance imaging system with the pulse sequence instructions;
- reconstructing one or more sequential images from the sequential magnetic resonance data;
- computing a distance measure between the one or more sequential images and each of the set of memory groups;
- assigning the one or more sequential images to an existing memory group if the distance measure between the existing memory group and the one or more sequential images is within a predetermined range;

creating a subsequent memory group in the memory if the one or more sequential images is not assigned to the chosen memory group; and assigning the one or more sequential image to the subsequent memory group if the subsequent memory group is created.

\* \* \* \* \*